United States Patent
Takeda et al.

(10) Patent No.: US 7,998,100 B2
(45) Date of Patent: Aug. 16, 2011

(54) APPARATUS FOR DENATURATING BILIRUBIN AND BILIRUBIN DIALYZER

(75) Inventors: Yoshimasa Takeda, Okayama (JP); Kiyoshi Morita, Okayama (JP)

(73) Assignee: National University Corporation Okayama University, Okayama (JP)

( * ) Notice: Subject to any disclaimer, the term of this patent is extended or adjusted under 35 U.S.C. 154(b) by 709 days.

(21) Appl. No.: 11/988,195

(22) PCT Filed: Jun. 30, 2006

(86) PCT No.: PCT/JP2006/313155
§ 371 (c)(1), (2), (4) Date: Jan. 2, 2008

(87) PCT Pub. No.: WO2007/004593
PCT Pub. Date: Jan. 11, 2007

(65) Prior Publication Data
US 2009/0131771 A1 May 21, 2009

(30) Foreign Application Priority Data
Jul. 1, 2005 (JP) .................. 2005-194414

(51) Int. Cl.
*A61M 37/00* (2006.01)

(52) U.S. Cl. ....... 604/6.09; 604/5.04; 604/6.1; 604/6.01

(58) Field of Classification Search .................. 210/645, 210/646; 604/4.01, 5.01, 5.04, 6.08, 6.09
See application file for complete search history.

(56) References Cited

U.S. PATENT DOCUMENTS

| | | | | |
|---|---|---|---|---|
| 4,350,156 A * | 9/1982 | Malchesky et al. | .......... | 604/6.04 |
| 5,536,238 A * | 7/1996 | Bischof | ............ | 604/5.04 |
| 6,918,886 B1 * | 7/2005 | Baurmeister | ............ | 604/6.09 |
| 7,201,730 B2 * | 4/2007 | Davidner et al. | .......... | 604/6.08 |
| 2003/0219354 A1 | 11/2003 | Hlavinka et al. | | |
| 2005/0015040 A1 * | 1/2005 | Wuepper | ............ | 604/5.01 |

FOREIGN PATENT DOCUMENTS

| | | |
|---|---|---|
| EP | 1481700 | 12/2004 |
| JP | 63-275351 | 11/1988 |
| JP | 8-131543 | 5/1996 |
| JP | 9-38221 | 2/1997 |
| JP | 2004-223435 | 8/2004 |
| JP | 2004-358243 | 12/2004 |
| JP | 2005-516978 | 6/2005 |
| WO | WO-03/063915 | 8/2003 |

* cited by examiner

*Primary Examiner* — Leslie R Deak
(74) *Attorney, Agent, or Firm* — Jordan and Hamburg LLP.

(57) ABSTRACT

The present invention provides a bilirubin reducing means which can minimize a risk such as the onset of an infection or the occurrence of blood coagulation and can reduce physical, temporal and economical burdens imposed on a patient suffering from liver dysfunction. A bilirubin denaturating apparatus includes a dialyzing portion which has a dialyzing column for performing dialysis of blood using hollow fibers incorporated therein; an infusion supply portion which supplies an infusion used for dialysis in the dialyzing portion to the dialyzing portion; and a blood circulating portion which feeds blood to the dialyzing portion and returns the blood dialyzed by the dialyzing portion, wherein the dialyzing portion includes a radiation means which radiates green light to the hollow fibers, and the radiation means radiates the green light to the hollow fibers for converting fat-soluble bilirubin in the blood flowing in the inside of the hollow fibers into water-soluble bilirubin thus eluting the water-soluble bilirubin in the infusion.

3 Claims, 4 Drawing Sheets

APPARATUS FOR DENATURATING BILIRUBIN AND BILIRUBIN DIALYZER

BACKGROUND OF THE INVENTION

The present invention relates to a bilirubin denaturating apparatus and a bilirubin dialyzer used for blood treatment of a patient suffering from liver dysfunction whose function of converting fat-soluble bilirubin into water-soluble bilirubin is lowered due to a malfunction or a function failure of the liver.

Bilirubin which is generated by the decomposition of hemoglobin in erythrocyte in a living body usually is present in a form of fat-soluble bilirubin. This fat-soluble bilirubin is converted into water-soluble bilirubin in a liver. Further, the water-soluble bilirubin is strained from blood as a waste product in a kidney and is discharged to the outside of the living body.

Accordingly, when a malfunction or a function failure of a liver occurs, the liver cannot convert fat-soluble bilirubin into water-soluble bilirubin and hence, fat-soluble bilirubin is accumulated in the inside of the living body and so-called symptoms of jaundice appear. Accordingly, a cure or a treatment for converting fat-soluble biliru bin into water-soluble bilirubin becomes necessary.

It has been known that fat-soluble bilirubin is converted into water-soluble bilirubin by radiating green light having a wavelength of 450 nm to 530 nm to fat-soluble bilirubin. In view of the above, there has been proposed a device which radiates green light to a patient suffering from liver dysfunction whose function of converting fat-soluble bilirubin into water-soluble bilirubin is lowered using a light source which can radiate green light thus converting fat-soluble bilirubin in blood into water-soluble bilirubin with green light which permeates a skin (see, patent document 1, for example).

However, since a body surface area per weight is small in the case of an adult, the conversion efficiency from fat-soluble bilirubin into water-soluble bilirubin with the radiation of green light is extremely low. In this manner, the method disclosed in patent document 1 is not a realistic bilirubin reducing method.

In view of the above, currently, a blood plasma exchange method which reduces the bilirubin concentration by exchanging plasma in blood or a bilirubin absorption method which reduces the bilirubin concentration by absorbing and removing bilirubin using a bilirubin absorption column has been put into practice. Further, as another method, there has been also proposed a method which performs the conversion of fat-soluble bilirubin into water-soluble bilirubin by circulating blood such that a portion of blood is extracted from a patient suffering from liver dysfunction, green light is directly radiated to the blood and, thereafter, the blood is made to return to the inside of a living body (see patent document 2, for example).

Patent document 1: JP-A-09-038221
Patent document 2: JP-A-2004-358243

SUMMARY OF THE INVENTION

However, in the case of the blood exchange method, it is necessary to perform the blood transfusion of plasma from other people and hence, there exists a risk of infection due to the blood transfusion. On the other hand, in the case of the bilirubin absorption method, there exists a risk that a coagulating system or an immune system in the blood is activated thus giving rise to the coagulation of blood or an inflammatory reaction.

Further, in the blood circulation bilirubin denaturating method, there exists a drawback that large physical, temporal and economical burdens are imposed on a patient suffering from liver dysfunction who takes the cure.

In this manner, in reducing bilirubin, there has been a demand for a curing method which can reduce the risk such as infection or blood coagulation as much as possible and, at the same time, can reduce physical, temporal and economical burdens imposed on the patient suffering from liver dysfunction.

Inventors of the present invention have focused their attention on a fact that, in many cases, many patients suffering from liver dysfunction whose conversion efficiency of bilirubin is lowered also suffer from kidney dysfunction and require artificial dialysis. Based on such a finding, the inventors of the present invention have arrived at the possibility of largely reducing burdens imposed on the patient suffering form liver dysfunction while reducing a risk by performing the denaturation of bilirubin along with artificial dialysis.

According to a bilirubin denaturating apparatus of the present invention, the bilirubin denaturating apparatus which converts fat-soluble bilirubin in blood into water-soluble bilirubin by radiating green light to the blood includes a plurality of hollow fibers which allows the blood to flow therethrough, a plurality of light transmitting fiber bodies or light transmitting planar bodies which is arranged along the hollow fibers and radiate green light to the hollow fibers, and a cylindrical frame which allows the insertion of the hollow fibers and the light transmitting fiber bodies or the light transmitting planar bodies therein and mounts a first end frame and a second end frame on ends thereof, wherein the bilirubin denaturating apparatus radiates the green light to the hollow fibers from the light transmitting fiber bodies or the light transmitting planar bodies while supplying an infusion used for dialysis of the liquid into the cylindrical frame thus dissolving the water-soluble bilirubin into the infusion while dialyzing the blood.

Further, the bilirubin denaturating apparatus of the present invention is also characterized in that the cylindrical frame includes an infusion inlet to which an infusion feed pipe for supplying the infusion into the inside of the cylindrical frame is connected, and an infusion outlet to which an infusion discharge pipe for discharging the infusion in the inside of the cylindrical frame is connected, and a light guide pipe which connects the infusion inlet or the infusion outlet to the light transmitting fiber body or the light transmitting planar body is inserted into the inside of the cylindrical frame.

According to the bilirubin dialyzer of the present invention, the bilirubin dialyzer includes the bilirubin denaturating apparatus described hereinabove, an infusion supply portion for supplying an infusion to the bilirubin denaturating apparatus, and a light source of green light for radiating green light from the light transmitting fiber body or a light transmitting planar body of the bilirubin denaturating apparatus.

According to the present invention, the plurality of hollow fibers which allows the blood to flow therethrough and the plurality of light transmitting fiber bodies or light transmitting planar bodies which is arranged along the hollow fibers and radiate green light to the hollow fibers are inserted into the cylindrical frame, and the dialysis of the blood is performed with the infusion fed to the cylindrical frame while radiating the green light to the hollow fibers from the light transmitting fiber bodies or the light transmitting planar bodies and hence, the green light can be radiated to the blood while increasing a surface area of the blood by the hollow fibers whereby the conversion efficiency of the fat-soluble bilirubin into the water-soluble bilirubin can be extremely enhanced and, at the same time, the fat-soluble bilirubin can be converted into the water-soluble bilirubin together with an artificial dialysis.

Further, by inserting the light guide pipe which is connected with the light transmitting fiber bodies or the light transmitting planar bodies and guides the green light into the inside of the cylindrical frame from the infusion inlet or the infusion outlet formed in the cylindrical frame, it is possible to prevent the occurrence of a drawback such as the coagulation of the blood.

Further, the bilirubin dialyzer of the present invention includes the bilirubin denaturating apparatus described hereinabove, the infusion supply portion for supplying the infusion to the bilirubin denaturating apparatus, and the light source of green light for radiating the green light from the light transmitting fiber body or the light transmitting planar body of the bilirubin denaturating apparatus and hence, two cures consisting of the artificial dialysis and the bilirubin dialysis can be performed simultaneously whereby physical burden imposed on the patient suffering from dysfunction can be largely reduced.

DETAILED DESCRIPTION OF THE INVENTION

A bilirubin denaturating apparatus and a bilirubin dialyzer of the present invention are configured such that light for converting fat-soluble bilirubin into water-soluble bilirubin is radiated to a dialyzing column used for artificial dialysis from a radiation means which radiates such a light thus converting fat-soluble bilirubin in blood which flows in the inside of hollow fibers incorporated in the dialyzing column into water-soluble bilirubin.

By radiating light to the hollow fibers in this manner, it is possible to substantially directly radiate light to the blood and, at the same time, a surface area of the blood is increased due to the hollow fibers and hence, the radiation efficiency can be enhanced whereby fat-soluble bilirubin can be efficiently converted into water-soluble bilirubin.

It is sufficient that the radiated light is light of blue, bluish green or green having a wavelength ranging from 400 to 550 nm, and the radiated light may preferably be green light having a wavelength ranging from 450 nm to 530 nm or light having a wavelength around such a wavelength range. In this specification, for facilitating the explanation of the present invention, light having the wavelength ranging from 400 to 550 nm is referred to as green light. A light source of green light may be formed by covering a light source such as a fluorescent lamp with a green color film or may be formed of a xenon lamp or a laser beam source.

By converting fat-soluble bilirubin into water-soluble bilirubin with the radiation of green light to the dialyzing column used for artificial dialysis, the bilirubin dialysis can be performed together with the artificial dialysis performed as a cure for a patient suffering from kidney dysfunction and hence, it is possible to largely reduce physical, temporal and economical burdens imposed on a patient suffering from liver dysfunction who also suffers from kidney dysfunction.

Particularly, the bilirubin dialyzer which uses the bilirubin denaturating apparatus can treat a relatively large quantity of blood ranging from 100 to 200 ml per minute, for example, thus enhancing the treatment efficiency.

Further, the bilirubin dialyzer using the bilirubin denaturating apparatus can decrease a risk to a level of risk in artificial dialysis lower than a risk of infection in a conventional plasma exchange or a risk of blood coagulation in bilirubin absorption thus enabling the safe use of the bilirubin dialyzer by a person suffering from liver dysfunction.

Figure 1:
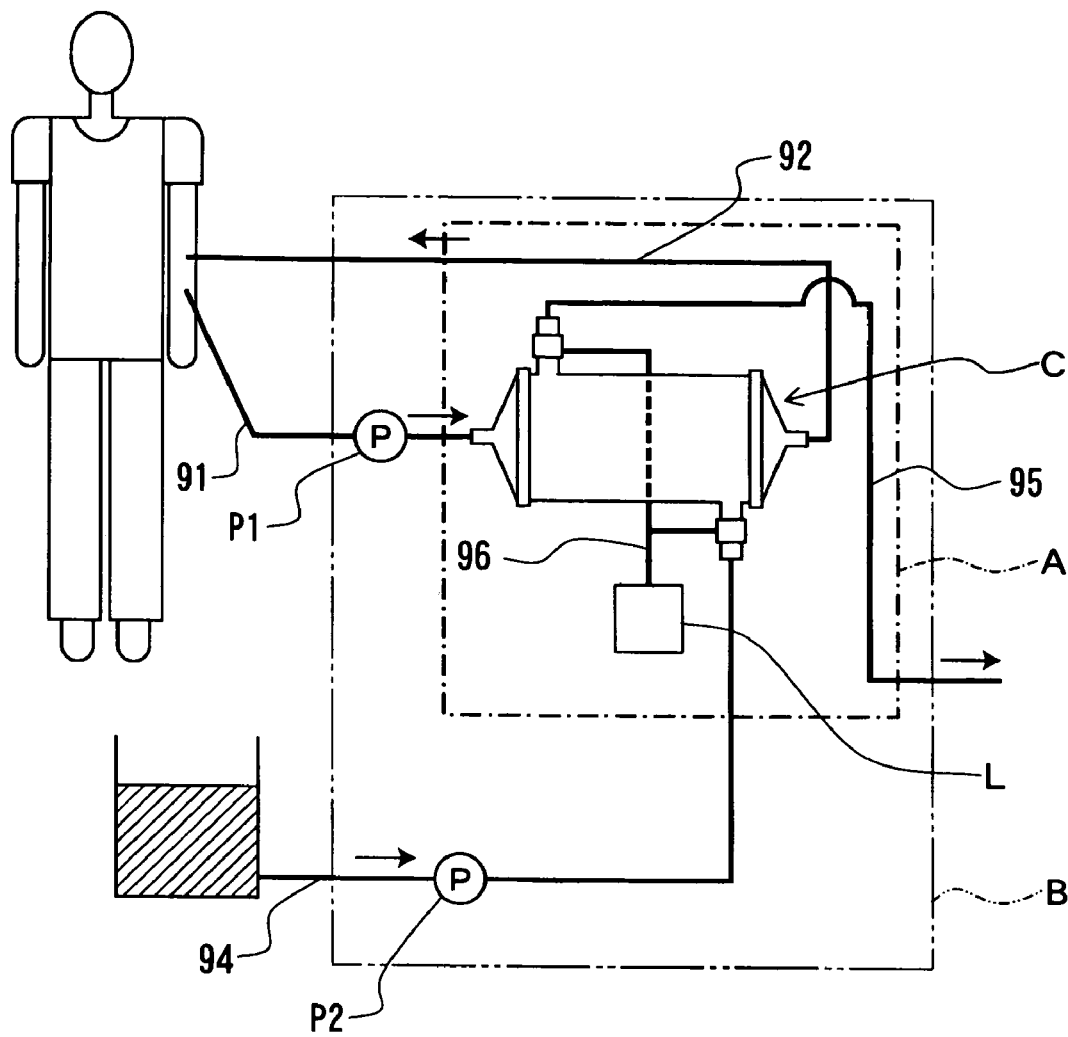
FIG. 1 is a schematic view of a bilirubin dialyzer provided with a bilirubin denaturating apparatus according to an embodiment of the present invention.

FIG. 1 is a schematic view of a bilirubin dialyzer B provided with a bilirubin denaturating apparatus A.

The bilirubin denaturating apparatus A includes a dialyzing column C which performs dialysis of blood using hollow fibers incorporated therein, and a light source device L which radiates green light to the hollow fibers of the dialyzing column C.

The bilirubin dialyzer B includes a blood feed pipe 91 which supplies blood sampled from a human body to the dialyzing column C by interposing a blood feed pump P1 in a middle portion thereof, a blood return pipe 92 which returns the blood treated by the dialyzing column C into the human body, an infusion feed pipe 94 which feeds an infusion used for performing dialysis by the dialyzing column C to the dialyzing column C from an infusion tank 93, and an infusion discharge pipe 95 which discharges the infusion after the infusion passes the dialyzing column C. An infusion feed pump P2 is interposed on a middle portion of the infusion feed pipe 94, and the infusion is fed to the dialyzing column C from the infusion tank 93 by the infusion feed pump P2.

To the blood feed pipe 91, the blood return pipe 92, the infusion feed pipe 94 and the infusion discharge pipe 95, a feed controller and a feed quantity detector and the like not shown in the drawing are respectively mounted when necessary so as to allow a control part not shown in the drawing to perform a proper dialysis.

In FIG. 1, numeral 96 indicates a light guide pipe made of an optical fiber for guiding green light radiated from the light source L to a light transmitting body mounted on the dialyzing column C as described later.

Figure 2:
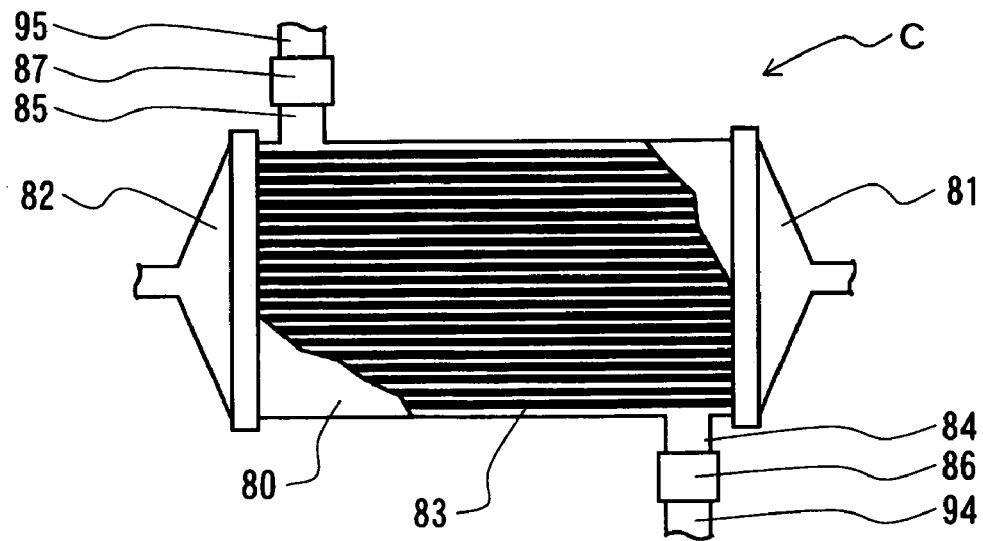
FIG. 2 is an explanatory view of a general-use dialyzing column.

The dialyzing column C is, as shown in FIG. 2, constituted by inserting a large number of hollow fibers 83 in the inside of a longitudinally elongated cylindrical frame 80, the cylindrical frame 80 forms a first end frame 81 to which one ends of the hollow fibers 83 are connected on one end thereof and a second end frame 82 to which other ends of the hollow fibers 83 are connected on the other end thereof, and the hollow fibers 83 extend between the first end frame 81 and the second end frame 82.

Further, the dialyzing column C can smoothly feed the blood fed to the first end frame 81 from the blood feed pipe 91 to the inside of the respective hollow fibers 83, and also can smoothly feed the blood fed to the second end frame 82 from the hollow fibers 83 to the blood return pipe 92 connected to the second end frame 82.

The inside of the cylindrical frame 80 is filled with the infusion fed from the infusion feed pipe 94 and the hollow fibers 83 are immersed into the infusion so as to perform the dialysis of the blood.

That is, an infusion inlet 84 which projects from a peripheral surface of the cylindrical frame 80 is formed in one end of the cylindrical frame 80, and an infusion outlet 85 which projects from the peripheral surface is formed in the other end of the cylindrical frame 80. An infusion feed pipe 94 is communicably connected with the infusion inlet 84 by way of a first connecting jig 86, and an infusion discharge pipe 95 is communicably connected with the infusion outlet 85 by way of a second connecting jig 87 whereby the infusion fed by the infusion feed pump P2 is fed to the inside of the cylindrical frame 80 from the infusion inlet 84 and the infusion is discharged to the outside of the cylindrical frame 80 from the infusion outlet 85.

In this manner, the bilirubin dialyzer B is basically equal to a conventional artificial dialyzer and only differs from the conventional artificial dialyzer with respect to a point that the bilirubin dialyzer B includes radiation means for radiating green light to the dialyzing column C as described later.

Hereinafter, the constitution of the bilirubin denaturating apparatus A which constitutes an essential part of the present invention is explained with respect to respective examples. Here, in the explanation made hereinafter, the hollow fibers 83 are omitted from drawings unless otherwise necessary.

Example 1

Figure 3:
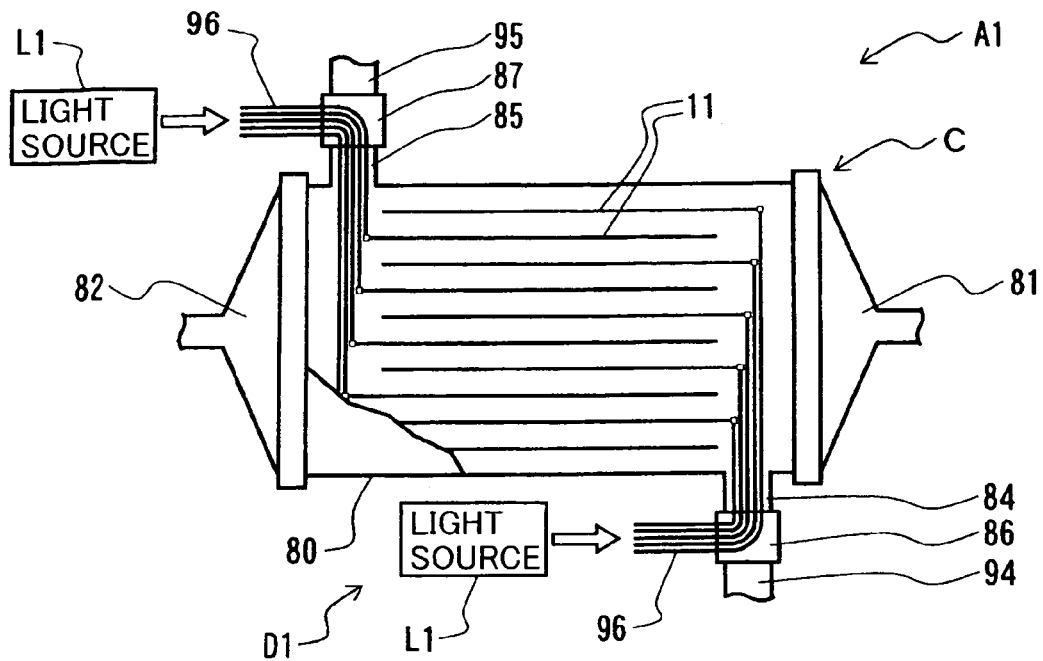
FIG. 3 is a schematic view of a bilirubin denaturating apparatus according to an example 1.

FIG. 3 is a schematic view of a bilirubin denaturating apparatus A1 of an example 1, wherein the bilirubin denaturating apparatus A1 includes the above-mentioned dialyzing column C and a light radiating portion D1 which constitutes a radiation means for radiating green light to the hollow fibers 83 of the dialyzing column C.

The light radiating portion D1 includes a laser light source L1 for radiating light having a predetermined wavelength, light transmitting fiber bodies 11 which are formed of a fine-line-shaped light guide plate radiating light radiated from the laser light source L1 to the hollow fibers 83, and light guide pipes 96 which are formed of optical fibers guiding light to the light transmitting fiber bodies 11 from the laser light source L1.

The light transmitting fiber bodies 11 can scatter the light guided by the light guide pipe 96 and can radiate the light in the direction orthogonal to the longitudinal direction of the light transmitting fiber bodies 11. By arranging the light transmitting fiber bodies 11 along the hollow fibers 83, green light is radiated to the hollow fibers 83.

According to the bilirubin denaturating apparatus A1 of this example, a plurality of light transmitting fiber bodies 11 is arranged in the inside of the dialyzing column C at a predetermined interval, and the light guide pipe 96 are connected to the respective light transmitting fiber bodies 11.

Further, in the bilirubin denaturating apparatus A1 of this example, the light transmitting fiber body 11 has a diameter approximately equal to a diameter of the hollow fiber 83. However, the diameter of the light transmitting fiber body 11 may be set larger than the diameter of the hollow fiber 83 or may be set to a suitable value in view of the relationship with the number of arrangement of light transmitting fiber bodies 11.

Further, in the bilirubin denaturating apparatus A1 of this example, the respective light guide pipes 96 which are connected with the respective light transmitting fiber bodies 11 are inserted into the inside of the dialyzing column C from the first connecting jig 86 connected to the infusion inlet 84 or the second connecting jig 87 connected to the infusion outlet 85 and hence, the direct contact of the light transmitting fiber body 11 and the light guide pipes 96 with blood can be prevented thus preventing the occurrence of a drawback such as the coagulation of blood.

Particularly, in the bilirubin denaturating apparatus A1 of this example, the light guide pipes 96 which are connected to the respective light transmitting fiber bodies 11 are inserted through the infusion inlet 84 and the infusion outlet 85 of the dialyzing column C. However, depending on the number of arrangement of the light transmitting fiber bodies 11, the light guide pipes 96 may be inserted into the inside of the dialyzing column C only through either one of the infusion inlet 84 and the infusion outlet 85.

As in the case of this example, by arranging the light transmitting fiber bodies 11 which radiate green light in the inside of the dialyzing column C along the hollow fibers 83, it is possible to radiate green light also to the hollow fibers 83 positioned at a center portion of the dialyzing column C thus enhancing the radiation efficiency.

Particularly, when the plurality of hollow fibers 83 is arranged around the light transmitting fiber bodies 11 such that the light transmitting fiber bodies 11 are surround by the hollow fibers 83, the whole green light radiated from the light transmitting fiber bodies 11 are absorbed in the blood and hence, the radiation efficiency can be further enhanced.

In the dialyzing column C of this example, the hollow fibers 83 and the light transmitting fiber bodies 11 are mounted on the dialyzing column C separately from each other. However, the light transmitting fiber bodies and the hollow fibers may be integrally formed by joining the light transmitting fiber bodies to the hollow fibers along with the formation of the hollow fibers or a portion of the hollow fiber may be formed of the light transmitting fiber body, or a portion of a periphery of the hollow fiber maybe covered with a light guiding plate material which constitutes the light transmitting fiber body.

EXAMPLE 2

Figure 4:
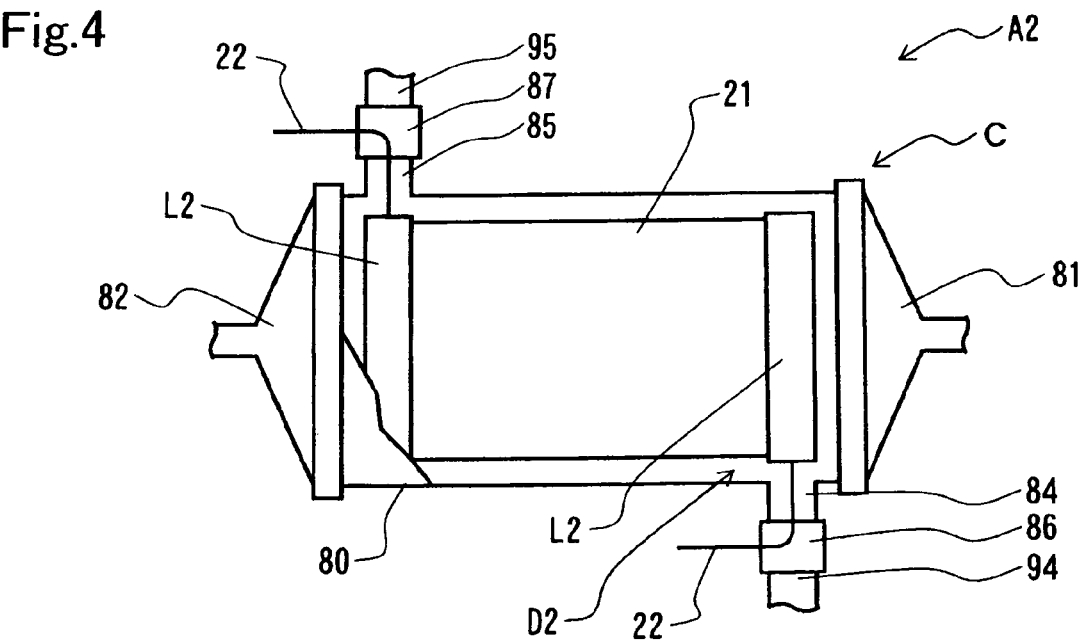
FIG. 4 is a schematic view of a bilirubin denaturating apparatus according to an example 2.

FIG. 4 is a schematic view of a bilirubin denaturating apparatus A2 of an example 2, wherein the bilirubin denaturating apparatus A2 includes the above-mentioned dialyzing column C, and a light radiating portion D2 which constitutes a radiation means for radiating green light to the hollow fibers 83 of the dialyzing column C.

The light radiating portion D2 includes an LED light source L2 which incorporates an LED (Light Emitting Diode) emitting green light, and a light transmitting planar body 21 formed of a planar light guide plate which radiates the light radiated from the LED light source L2 toward the hollow fibers 83. In FIG. 4, numeral 22 indicates an electricity supply line which supplies electricity to the LED light source L2.

The light transmitting planar body 21 can scatter the green light radiated from the LED light source L2 and can radiate the light in the direction orthogonal to the longitudinal direction of the light transmitting planar body 21. The light transmitting planar body 21 is arranged along the hollow fibers 83 so as to radiate green light to the hollow fibers 83. That is, the light radiating portion D2 forms a so-called backlight.

In the bilirubin denaturating apparatus A2 of this example, the light transmitting planar body 21 is constituted of a single light guide plate. However, when necessary, a reflective film may be mounted on the light transmitting planar body 21 so as to enhance the radiation efficiency.

Further, in the bilirubin denaturating apparatus A2 of this example, although the LED light source L2 is connected to both ends of the light transmitting planar body 21 respectively, the LED light source L2 may be connected to only one end of the light transmitting planar body 21.

Further, in the bilirubin denaturating apparatus A2 of this example, the light transmitting planar body 21 has a planar shape having a large area. However, slits for allowing the infusion to flow therethrough may be formed in the light transmitting planar body 21 at a predetermined interval or planar plates having a fine width may be arranged on a plane in a spaced-apart manner at a predetermined interval.

Besides a case in which only one light transmitting planar body 21 is arranged in the inside of the dialyzing column C, a plurality of light transmitting planar bodies 21 may be arranged at a predetermined interval and, at the same time, the hollow fibers 83 may be arranged between the respective light transmitting planar bodies 21. In this case, the radiation efficiency of green light can be enhanced.

The electricity supply line 22 connected to the LED light source L2 is introduced into the inside of the dialyzing column C from the first connecting jig 86 connected to the infusion inlet 84 and the second connecting jig 87 connected to the infusion outlet 85 and hence, the direct contact of the LED light source L2 and the light transmitting planar body 21 with blood can be prevented thus preventing the occurrence of the drawback such as the coagulation of blood.

In this manner, by arranging the light transmitting planar body 21 of the light radiating portion D2 in the inside of the dialyzing column C along the hollow fibers 83, the light transmitting body can be extremely easily arranged in the inside of the dialyzing column C thus suppressing the increase of a cost of the dialyzing column C.

EXAMPLE 3

Figure 5:
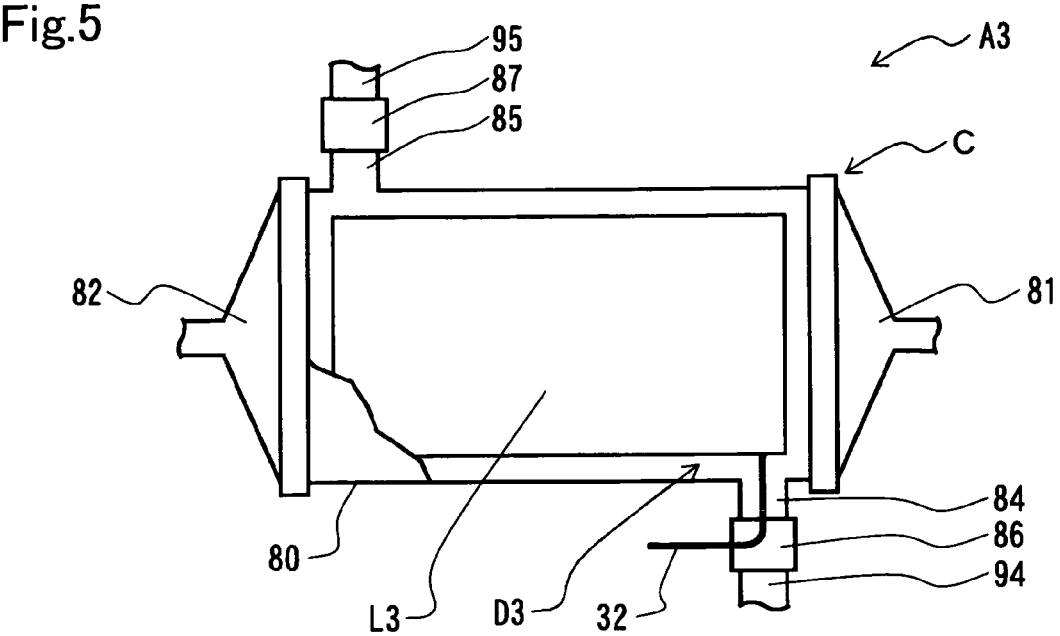
FIG. 5 is a schematic view of a bilirubin denaturating apparatus according to an example 3.

FIG. 5 is a schematic view of a bilirubin denaturating apparatus A3 of an example 3, wherein the bilirubin denaturating apparatus A3 includes the above-mentioned dialyzing column C, and a light radiating portion D3 which constitutes a radiation means for radiating green light to the hollow fibers 83 of the dialyzing column C.

The light radiating portion D3 includes an organic EL light source L3 formed of a planar organic EL. In FIG. 5, numeral 32 indicates an electricity supply line which supplies electricity to the organic EL light source L3. That is, in the bilirubin denaturating apparatus A3 of this example, in place of the light transmitting planar body 21 and the LED light source L2 in the inside of the dialyzing column C of the bilirubin denaturating apparatus A2 of the example 2, the organic EL light source 13 is provided, and the organic EL light source L3 is arranged along the hollow fibers 83.

As the organic EL light source L3, an organic EL light source which emits green light is used. Although the organic EL light source L3 may increase an area thereof as large as possible to enhance the conversion efficiency of bilirubin, when necessary, slits may be formed in the organic EL light source L3 at predetermined positions thus preventing the interruption of fluidity of infusion.

The electricity supply line 32 connected to the organic EL light source L3 is introduced into the inside of the dialyzing column C from the first connecting jig 86 connected to the infusion inlet 84 and hence, the direct contact of the organic EL light source L3 with blood can be prevented thus preventing the occurrence of the drawback such as the coagulation of blood.

Besides a case in which only one organic EL light source L3 is arranged in the inside of the dialyzing column C, a plurality of organic EL light sources L3 may be arranged at a predetermined interval and, at the same time, the hollow fibers 83 maybe arranged between the respective organic EL light sources L3. In this case, the radiation efficiency of green light can be enhanced.

In this manner, by arranging the organic EL light source L3 of the light radiating portion D3 in the inside of the dialyzing column C substantially parallel to the hollow fibers 83, the light source can be extremely easily arranged in the inside of the dialyzing column C thus suppressing the increase of a cost of the dialyzing column C.

EXAMPLE 4

Figure 6:
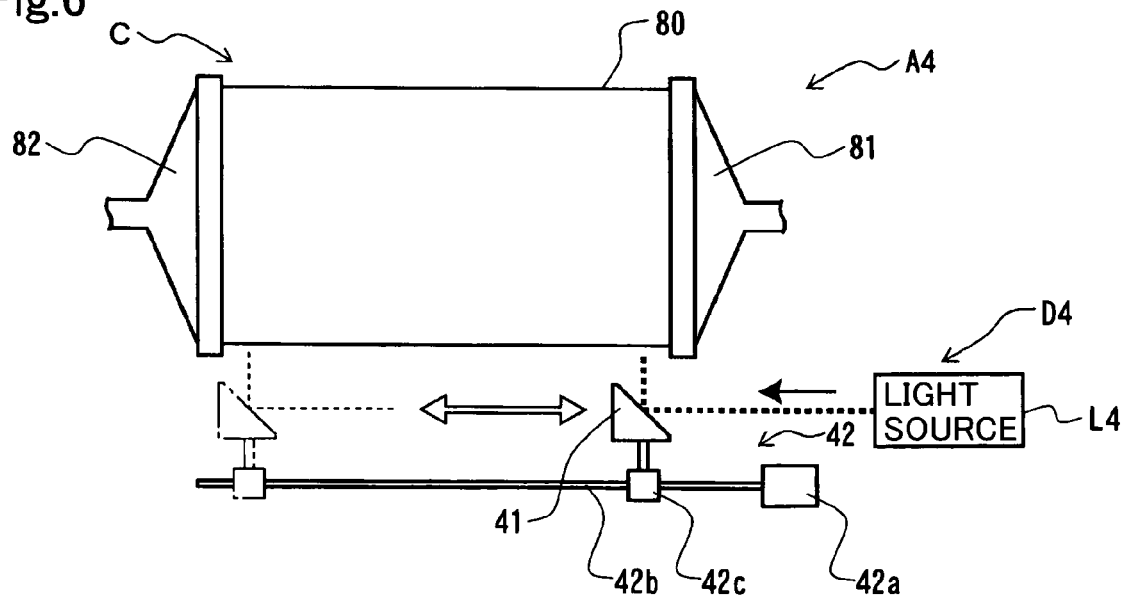
FIG. 6 is a schematic view of a bilirubin denaturating apparatus according to an example 4.

FIG. 6 is a schematic view of a bilirubin denaturating apparatus A4 of an example 4, wherein the bilirubin denaturating apparatus A4 includes the above-mentioned dialyzing column C, and a light radiating portion D4 which constitutes a radiation means for radiating green light to the hollow fibers 83 of the dialyzing column C.

The light radiating portion D4 is constituted of a laser light source L4 which radiates light having a predetermined wavelength, a tilting radiation adjusting body 41 which adjusts the radiating direction of light radiated from the laser light source L4, and a tilting manipulating portion 42 which performs a tilting manipulation of the tilting radiation adjusting body 41.

The tilting radiation adjusting body 41 is constituted of a mirror which reflects the light incident from the laser light source L4 in the predetermined radiating direction.

The tilting manipulation portion 42 is constituted of a drive motor 42a, a rod-shaped helical body 42b which is interlockingly connected with an output shaft of the drive motor 42a, and a support body 42c which is threadedly engaged with the helical body 42b.

The tilting radiation adjusting body 41 is mounted on the support body 42c. By rotating the helical body 42b in the normal direction or in the reverse direction by the drive motor 42a, the support body 42c is tilted in a reciprocating manner along the helical body 42b, and the tilting radiation adjusting body 41 is tilted in a reciprocating manner along the helical body 42b corresponding to the reciprocating tilting of the helical body 42b.

The helical body 42b of this example is arranged along the hollow fibers 83 of the dialyzing column C thus tilting a radiation range of the laser beams reflected by the tilting radiation adjusting means 41 in the longitudinal direction of the hollow fibers 83.

In this manner, by radiating green light from the light radiating portion D4 arranged outside the dialyzing column C, it is possible to perform the radiation of green light at a relatively low cost.

Particularly with the use of the laser light source L4 of high output as a light source, green light having a wavelength most effective in the conversion of fat-soluble bilirubin into water-soluble bilirubin can be radiated toward the hollow fibers 83.

By performing the reciprocating tilting of the tilting radiation adjusting body 41 in the light radiating portion D4, even when the laser beams of relatively high output are radiated to the hollow fibers 83, it is possible to eliminate a possibility of damaging the hollow fibers 83. Here, this example is not limited to a case in which the light radiating portion D4 uses only one laser light source L4, and a plurality of laser light sources L4 may be arranged in the light radiating portion D4.

Example 5

Figure 7:
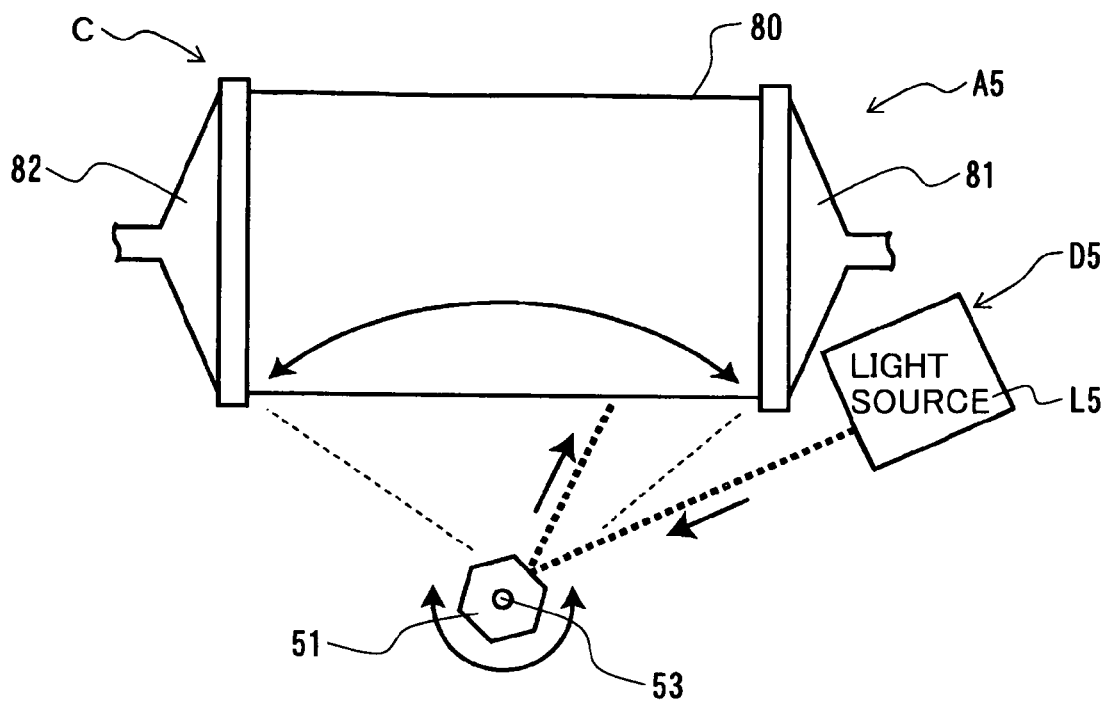
FIG. 7 is a schematic view of a bilirubin denaturating apparatus according to an example 5.

FIG. 7 is a schematic view of a bilirubin denaturating apparatus A5 of an example 5, wherein the bilirubin denaturating apparatus A5 includes the above-mentioned dialyzing column C, and a light radiating portion D5 which constitutes a radiation means for radiating green light to the hollow fibers 83 of the dialyzing column C.

The light radiating portion D5 is constituted of a laser light source L5 which radiates light having a predetermined wavelength, a rotary radiation adjusting body 51 which adjusts the radiating direction of light radiated from the laser light source L5, and a rotary manipulating portion (not shown in the drawing) which performs a rotary manipulation of the rotary radiation adjusting body 51.

The rotary radiation adjusting body 51 is formed of a polygonal-column-shaped mirror body which reflects laser beams radiated from the laser light source L5 in the predetermined radiating direction. In this example, the rotary radiation adjusting body 51 is formed of a hexagonal-column-shaped rotary radiation adjusting body 51 which has a peripheral surface thereof constituted of six planar mirror surfaces.

In the rotary manipulating portion, a rotary shaft 53 which is arranged on a center axis of the hexagonal-column-shaped rotary radiation adjusting body 51 is rotatably driven at a predetermined angular speed thus rotating the rotary radiation adjusting body 51. Due to such rotation of the rotary radiation adjusting body 51, a region radiated with the laser beam reflected on the rotary radiation adjusting body 51 is scanned in the longitudinal direction of the hollow fibers 83.

In this manner, by radiating green light from the light radiating portion D5 arranged outside the dialyzing column C, it is possible to perform the radiation of green light at a relatively low cost.

Particularly, with the use of the laser light source L5 of high output as a light source, green light having a wavelength most effective in the conversion of fat-soluble bilirubin into water-soluble bilirubin can be radiated toward the hollow fibers 83.

In the light radiating portion D5, the radiated area is scanned in the longitudinal direction of the follow fibers by rotating the rotary radiation adjusting body 51 and hence, even when the laser beams of relatively high output are radiated to the hollow fibers 83, it is possible to eliminate a possibility of damaging the hollow fibers 83. Here, this example is not limited to a case in which the light radiating portion D5 arranges only one laser light source L5, and a plurality of laser light sources L5 may be arranged in the light radiating portion D5. Example 6

Figure 8:
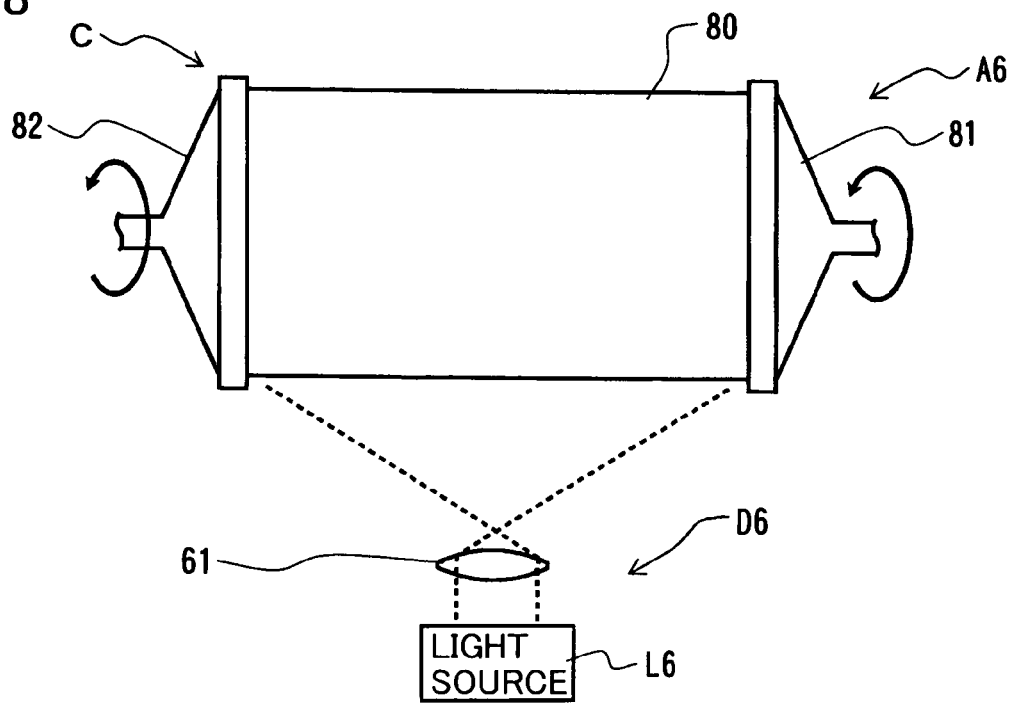
FIG. 8 is a schematic view of a bilirubin denaturating apparatus according to an example 6.

FIG. 8 is a schematic view of a bilirubin denaturating apparatus A6 of an example 6, wherein the bilirubin denaturating apparatus A6 includes the above-mentioned dialyzing column C, and a light radiating portion D6 which constitutes a radiation means for radiating green light to the hollow fibers 83 of the dialyzing column C.

The light radiating portion D6 is constituted of a laser light source L6 which radiates light having a predetermined wavelength, and a diffusion lens 61 which diffuses light radiated from the laser light source L6 and radiates the diffused light toward the hollow fibers 83. This diffusion lens 61 forms the radiation adjusting body which adjusts the radiating direction of the light.

Further, in the bilirubin denaturating apparatus A6 of this example, the dialyzing column C is rotatably driven at a predetermined angular velocity. By rotating the dialyzing column C relative to the diffusion lens 61 which forms the radiation adjusting body, green light is radiated to the whole surface of the dialyzing column C.

As a case opposite to the above-mentioned case, the light radiating portion D6 may be configured to be rotated in the circumferential direction of the dialyzing column C. By allowing the diffusion lens 61 which forms the radiation adjusting body to relatively rotate along a peripheral surface of the dialyzing column C, it is possible to radiate green light having a wavelength most effective in the conversion of fat-soluble bilirubin into water-soluble bilirubin toward every corner of the hollow fibers 83.

In this case, it is desirable to arrange the hollow fibers 83 in the dialyzing column C such that the hollow fibers 83 are arranged in a cylindrical shape along an inner peripheral surface of the cylindrical frame 80 of the dialyzing column C, and the hollow fibers 83 are not arranged in a center portion of the dialyzing column C at which the green light does not arrive.

The bilirubin denaturating apparatus is formed by providing the radiation means which radiates green light to the dialyzing column used for dialysis. By converting fat-soluble bilirubin in blood into water-soluble bilirubin along with dialysis, it is possible to enhance the conversion efficiency of bilirubin and, at the same time, no large physical burden is imposed on a patient suffering from liver dysfunction who requires the removal treatment of bilirubin in blood thus providing a cure method which can perform the dialysis of fat-soluble bilirubin together with the artificial dialysis.

The invention claimed:

1. A bilirubin denaturating apparatus that converts fat-soluble bilirubin in blood into water-soluble bilirubin by radiating green light to the blood, the bilirubin denaturating apparatus comprising:
   a cylindrical frame of a dialyzing column which includes a first end frame to which a blood feed pipe is connected and a second end frame to which a blood return pipe is connected, the cylindrical frame including an infusion inlet for denaturating which projects from a peripheral surface of the cylindrical frame at a first frame position and an infusion outlet for denaturating which projects from the peripheral surface of the cylindrical frame at a second frame position disposed away from the first frame position;
   a plurality of hollow fibers which are disposed inside of the cylindrical frame, the hollow fibers allowing the blood to flow therethrough, the hollow fibers having respective ends thereof communicating with the blood feed pipe and the blood return pipe by way of the first and second ends of the cylindrical frame;
   a plurality of light transmitting fiber bodies which are disposed inside of the cylindrical frame and being arranged along the hollow fibers, the light transmitting fiber bodies capable of radiating green light to the hollow fibers, each light transmitting fiber body being surrounded by the plurality of hollow fibers;
   a light source generating the green light; and
   light guide pipes inserted inside the cylindrical frame, the light guide pipes being inserted inside the cylindrical frame through both the infusion inlet and the infusion outlet, the light guide pipes having one end thereof connected to the light source and another end thereof connected to the light transmitting fiber bodies respectively, whereby
   the bilirubin denaturating apparatus is capable of radiating the green light to the hollow fibers from the light transmitting fiber bodies while supplying an infusion used for dialysis of the blood into the cylindrical frame, thus dissolving the water-soluble bilirubin into the infusion while dialyzing the blood.

2. A bilirubin denaturating apparatus that converts fat-soluble bilirubin in blood into water-soluble bilirubin by radiating green light to the blood, the bilirubin denaturating apparatus comprising:

a cylindrical frame of a dialyzing column which includes a first end frame to which a blood feed pipe is connected and a second end frame to which a blood return pipe is connected, the cylindrical frame including an infusion inlet for denaturating which projects from a peripheral surface of the cylindrical frame at a first frame position and an infusion outlet for denaturating which projects from the peripheral surface of the cylindrical frame at a second frame position disposed away from the first frame position:

a plurality of hollow fibers disposed inside of the cylindrical frame, the hollow fibers allowing the blood to flow therethrough, the hollow fibers having respective ends thereof communicating with the blood feed pipe and the blood return pipe by way of the first and second ends of the cylindrical frame;

a plurality o flight transmitting fiber bodies which are disposed inside of the cylindrical frame and being arranged along the hollow fibers, each light transmitting fiber body being integrally formed with each hollow fiber, the light transmitting fiber bodies capable of radiating green light to the hollow fibers;

a light source for generating the green light; and light guide pipes inserted inside the cylindrical frame, the light guide pipes being inserted inside the cylindrical frame through both the infusion inlet and the infusion outlet, the light guide pipes having a first end of the pipes connected to the light source and a second end of the pipes connected to the light transmitting fiber bodies, whereby the bilirubin denaturating apparatus is capable of radiating the green light to the hollow fibers fro in the light transmitting fiber bodies while supplying an infusion used for dialysis of the blood into the cylindrical frame, thus dissolving the water-soluble bilirubin into the infusion while dialyzing the blood.

3. A bilirubin dialyzer comprising:

the bilirubin denaturating apparatus of any one of claims 1 or 2; and an infusion supply portion for supplying the infusion to the bilirubin denaturating apparatus.

\* \* \* \* \*